United States Patent [19]

Boggess et al.

[11] Patent Number: 4,726,239
[45] Date of Patent: Feb. 23, 1988

[54] SOIL ANALYZER AND PENETRATOR

[75] Inventors: Ronald L. Boggess, Richmond; Lowell V. Babb; Alan G. Young, both of Sugar Land, all of Tex.

[73] Assignee: McClelland Engineers, Inc., Houston, Tex.

[21] Appl. No.: 13,749

[22] Filed: Feb. 9, 1987

[51] Int. Cl.$^4$ .............................................. G01N 33/42
[52] U.S. Cl. .......................................... 73/866; 73/84
[58] Field of Search ..................... 73/866, 84

[56] References Cited

U.S. PATENT DOCUMENTS

| 2,774,240 | 12/1956 | Fehlmonn | 73/84 |
| 3,331,240 | 7/1967 | Nilsson et al. | 73/84 |
| 4,433,737 | 2/1984 | Malloy | 73/84 X |

FOREIGN PATENT DOCUMENTS

| 1900339 | 2/1970 | Fed. Rep. of Germany | 73/84 |
| 1236655 | 6/1960 | France | 73/84 |
| 7805152 | 11/1978 | Netherlands | 73/84 |
| 398871 | 2/1974 | U.S.S.R. | 73/84 |
| 379174 | 1/1976 | U.S.S.R. | 73/84 |
| 642435 | 1/1979 | U.S.S.R. | 73/84 |

Primary Examiner—Tom Noland
Attorney, Agent, or Firm—Fulbright & Jaworski

[57] ABSTRACT

A soil analyzer and penetrator for driving into the ground, having a hydraulic ram with a longitudinal opening with a hollow tubing extending through the opening. A two-way chucking mechanism engages the outside of the tubing for driving the tubing into the ground and pulling the tubing from the ground. A coiling and straightening mechanism is positioned above the ram engaging the tubing for coiling the tubing as it is removed from the ground and straightening the tubing when it has been driven into the ground. A cone is connected to the bottom end of the tubing and may be of various types for measuring various ground parameters and inserting or removing materials into/from the ground.

9 Claims, 8 Drawing Figures

SOIL ANALYZER AND PENETRATOR

BACKGROUND OF THE INVENTION

It is well known to drive various instruments into the ground for measuring various parameters of the soil. However, such mechanisms are generally bulky, expensive and cumbersome to use.

The present invention is directed to an improved soil analyzer which is inexpensive to manufacture and to use and which is capable of making various soil measurements quickly and easily, as well as inserting or removing materials from the ground.

SUMMARY

The present invention is directed to a soil analyzer, for driving into the ground, and includes a hydraulic ram having a longitudinal opening therethrough. A hollow continuous tubing extends through the opening and a two-way chucking mechanism is connected to the ram and engages the outside of the tubing for driving the tubing into the ground and for pulling the tubing from the ground. A coiling and straightening mechanism is positioned above the ram engaging the tubing for coiling the tubing as it is removed from the ground to place it in a form for easy handling, and for straightening the tubing when it is being driven into the ground for reducing the possibility that the tubing will cause the driven hole to deviate from the vertical. Means are provided connected to the ram for holding the ram against the ground, and a cone is connected to the bottom end of the tubing for being driven into the ground.

A still further object of the present invention is wherein a tubular support is connected to the bottom of the ram and surrounds the cone and lower end of the tubing for insertion into the surface of the ground for protecting and directing the cone during penetration of hard ground surfaces.

Yet a still further object of the present invention is the provision of a buckling support positioned in the ram opening and around the tubing for supporting the tubing as it is driven downwardly. Preferably the buckling support includes split tubes having a shoulder for engaging a support in the ram.

Still a further object of the present invention is wherein the coiling and straightening mechanism includes four rollers with two of the rollers positioned on one side of the tubing and another two of the rollers positioned o the opposite side of the tubing.

Yet a further object of the present invention is wherein the cone includes a load cell body having first and second strain gauge load cells with a tip connected to the body for actuating the load cells for measuring the driving force on the cone tip and a sleeve is connected to the second load cell. The first load cell measures the driving force on the tip and the second load cell measures both the driving force on the tip and the friction of the ground on the sleeve.

Still a further object of the present invention is a cone angle measuring means connected to the cone and includes a light source and a light sensor with a concave lens positioned between the source and the sensor. A ball is movable on the concave lens and varies the amount of light transmitted to the sensor in proportion to the angle of the body.

Yet a still further object of the present invention is wherein the cone includes a body with a sleeve telescopically engaging the inside of the body in which the sleeve includes sampling openings. A cone tip is connected to the sleeve whereby the tip pushes the sleeve into the body when the tip is being driven into the ground and the tip extends the sleeve out of the body for obtaining fluid samples through the sleeve when the cone is pulled upwardly.

Other and further objects, features and advantages will be apparent from the following description of presently preferred embodiments of the invention, given for the purpose of disclosure and taken in conjunction with the accompanying drawings.

DESCRIPTION OF THE PREFERRED EMBODIMENT

Figure 1:
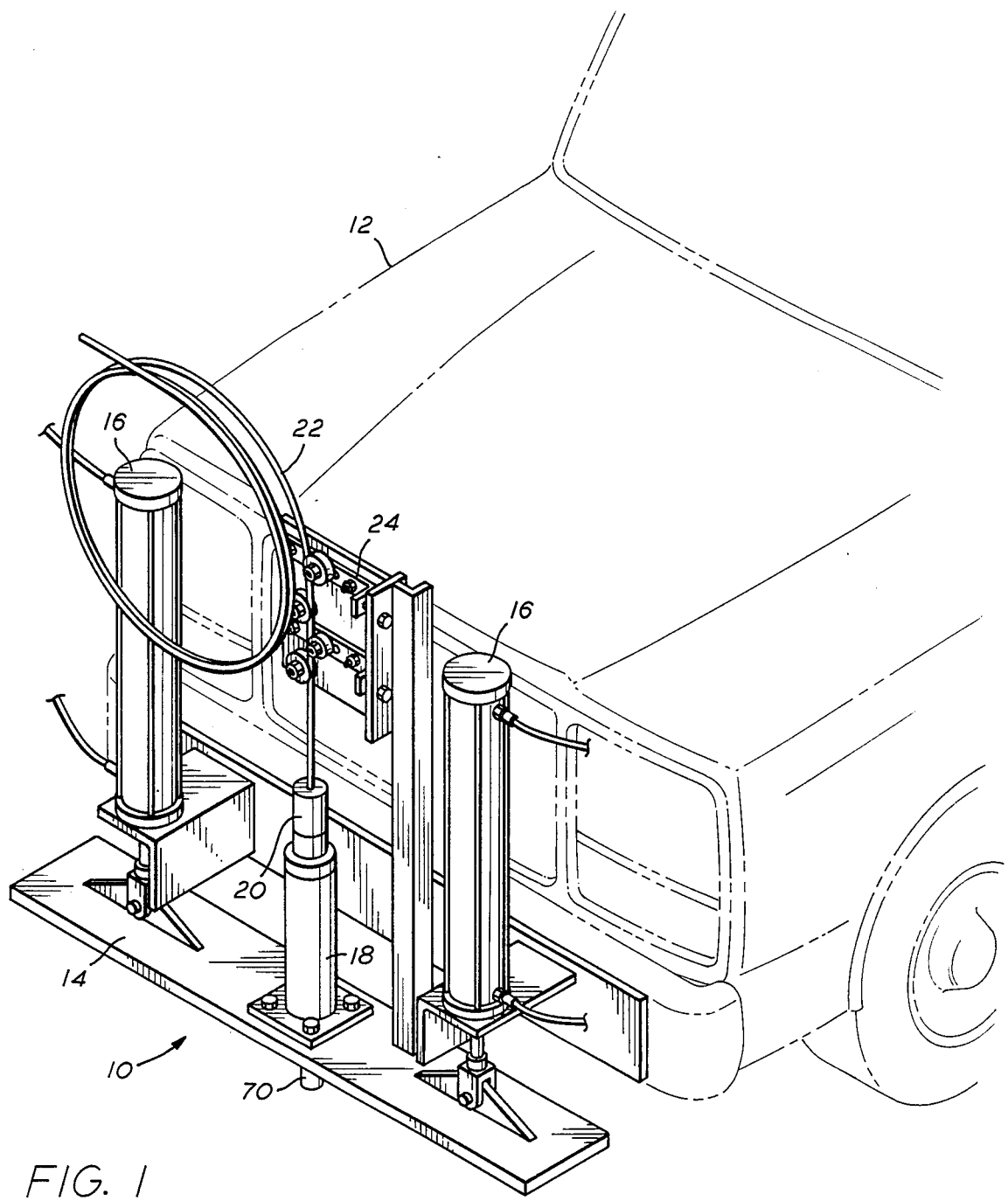
FIG. 1 is a perspective elevational view of the apparatus of the present invention shown attached to a vehicle.
Figure 2:
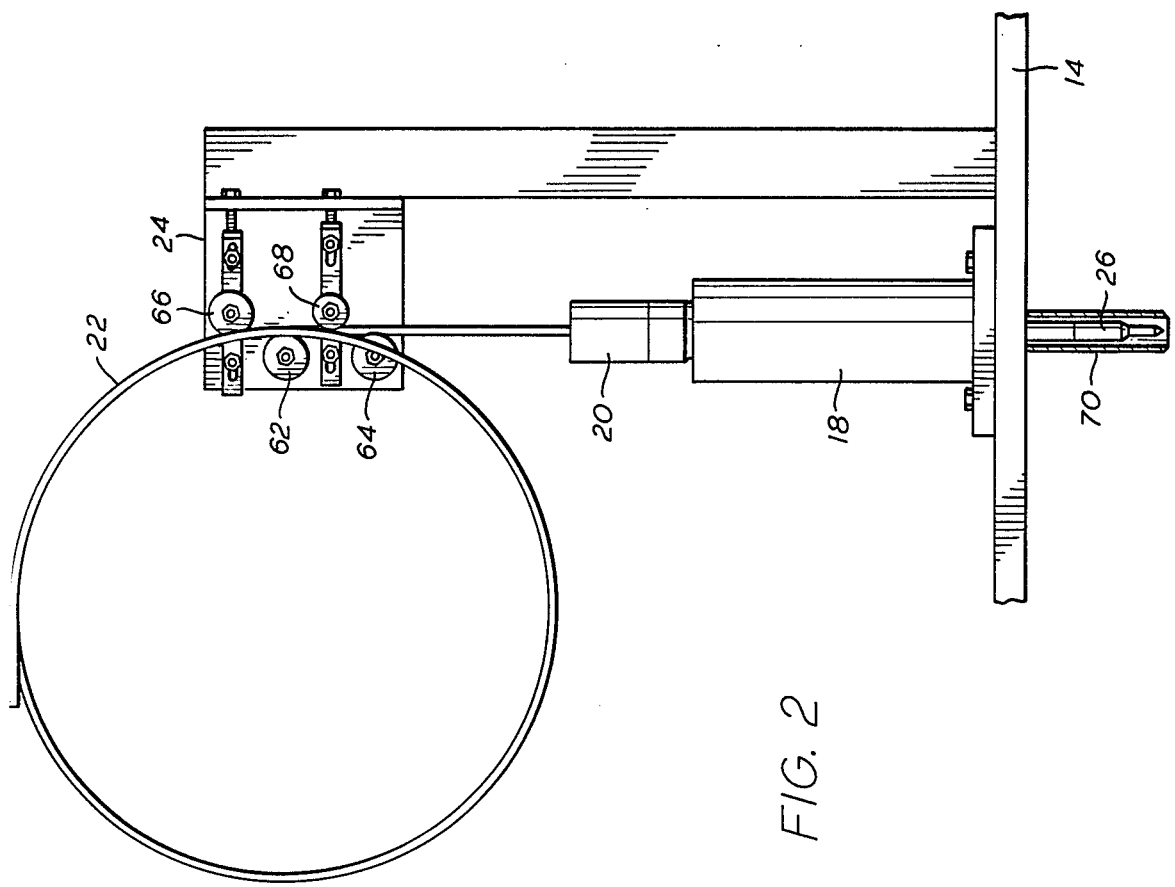
FIG. 2 is an enlarged fragmentary elevational view of the straightening mechanism, chucking mechanism and ram of the present invention.
Figures 6, 7, 8:
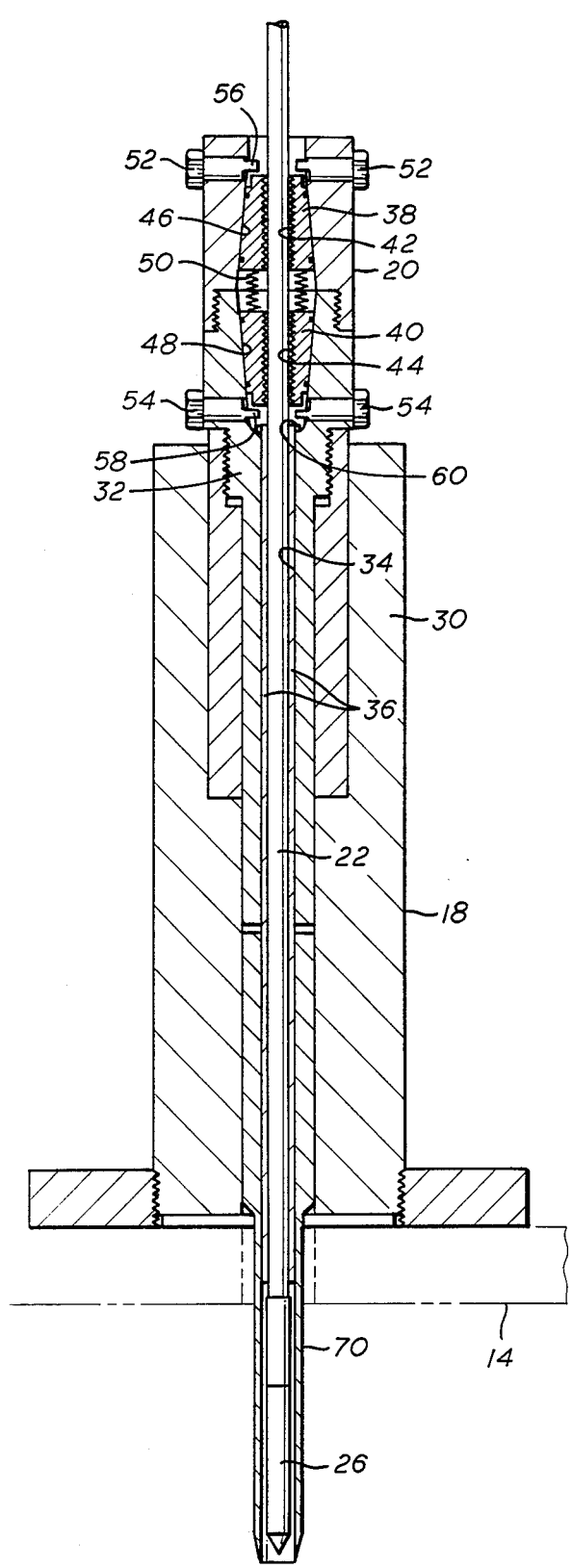
FIG. 6 is an enlarged fragmentary cross-sectional view of a tubing and cone positioned in the ram and chucking mechanism.
FIG. 7 is an enlarged cross-sectional view of one type of measuring cone connected to the bottom of the hollow tubing, and FIG. 8 an enlarged fragmentary cross-sectional view of another type of measuring sensor.

Referring now to the drawings, and particularly to FIGS. 1, 2 and 6, the reference numeral 10 generally indicates the soil analyzer of the present invention, here supported from a vehicle 12, and generally including a reaction plate 14 for being raised and lowered by hydraulic piston and cylinder assemblies 16, a hydraulic ram 18, a two-way chucking mechanism 20 for driving a hollow tube 22 into the ground and pulling the tubing 22 from the ground, and a tubing coiling and straightening mechanism 24. As best seen in FIGS. 2 and 6, a cone 26 is connected to the lower end of the tubing 22 for measuring various ground parameters.

Referring now to FIG. 6 the hydraulic ram 18 includes a cylinder 30 and ram 32 having a longitudinal opening 34 therethrough for accommodating the hollow tubing 22 and antibuckling supports 36.

The two-way chucking mechanism 20 is a device which grips the tubing 22 for pushing the tubing 22 downwardly into the ground and for pulling the tubing 22 upwardly from the ground. The mechanism 20 consists of a first chuck 38 and a second chuck 40. The chucks 38 and 40 are pie-shaped segments which are heat treated to achieve a hardness of approximately Rockwell C 60 and of which the inner surfaces include a pattern of serrations or teeth 42 and 44, respectively, for gripping the outside of the tubing 22. The chucks 38 and 40 are positioned in oppositely directed conical seats 46 and 48, respectively, with one or more compression springs 50 positioned between the chucks 38 and 40 to provide a pilot force to assist in initiating the gripping action. Rotatable cams 52 and 54 are provided for enabling the use of one of the chucks 38 and 40 at a time. For example, the cams 52 may be actuated to bring their eccentric ends 56 into engagement with the top chuck 38 forcing it downwardly in the conical seat 46 for disengaging the chuck 38 from the tubing 22. This causes the springs 50 to drive the lower chuck 40 into a tighter engagement with the tapered seat 48 and into a gripping relationship with the tubing 22. Therefore, on actuation of the hydraulic ram 30, the lower chuck 40 will act to pull the tubing 22 from the ground on the upward stroke of theram 30 but will release tne tubing 22 as the ram 30 moves downwardly, and on the next stroke upwardly will again grip the tubing 22 to provide another upward stroke for pulling the tubing 22 from the ground. Conversely, when the upper cams 52 are rotated to bring the eccentric lugs 56 out of engagement with the upper chuck 38 and the lower cams 54 are rotated to bring the eccentric lugs 58 into engagement with the lower chuck 40, the operation is reversed for allowing the hydraulic ram 30 to cause the chucking mechanism 20 to drive the tubing 22 into the ground.

The coacting surfaces of the tapered exterior of the chucks 38 and 40 and the seats 46 and 48, respectively, are preferably stainless steel and polished to allow the chucks 38 and 40 to slide easily in the seats so that very little force is needed to mobilize the gripping action of the chucks 38 and 40. Preferably, the angle is a five degree taper, but to prevent the tapered chucks 38 and 40 from locking in the seats 46 and 48 the exterior surface of the chucks 38 and 40 have a slight barrel shape at the end.

One of the advantages of the present soil analyzer 10 is the use of the small diameter coil tubing 22. The antibuckling supports 36 supports the external diameter of the tubing 22 to prevent buckling and preferably consist of two split tubes that are installed around the tubing 22 above the cone 26 so that they can be installed around the tubing 22. The antibuckling supports 36 include snoulders 60 at their upper ends for engaging the interior of the ram 32 for preventing the supports 36 from disengaging.

The hollow tubing 22 is preferably 3/8ths inch in diameter with a 1/8th inch hole through the center and provides a less expensive, ground penetration member which can be actuated by a simpler and less expensive ram 18 and chucking mechanism 20. However, the length of lhe tubing 22 may be 60 feet or longer as it is preferably a continuous tubing Therefore, for ease of handling and in transportation y a vehicle 12, a coiling and straightening mechanism 24 is utilized to coil the tubing 22 in a coil of approximatly two feet in diameter for ease of handling. In addition, the mechanism 22 straigntens the coil tubing as it is being driven into the ground to reduce the tendency of any set in the coil from deviating from the vertical as it is being driven.

Figure 4:
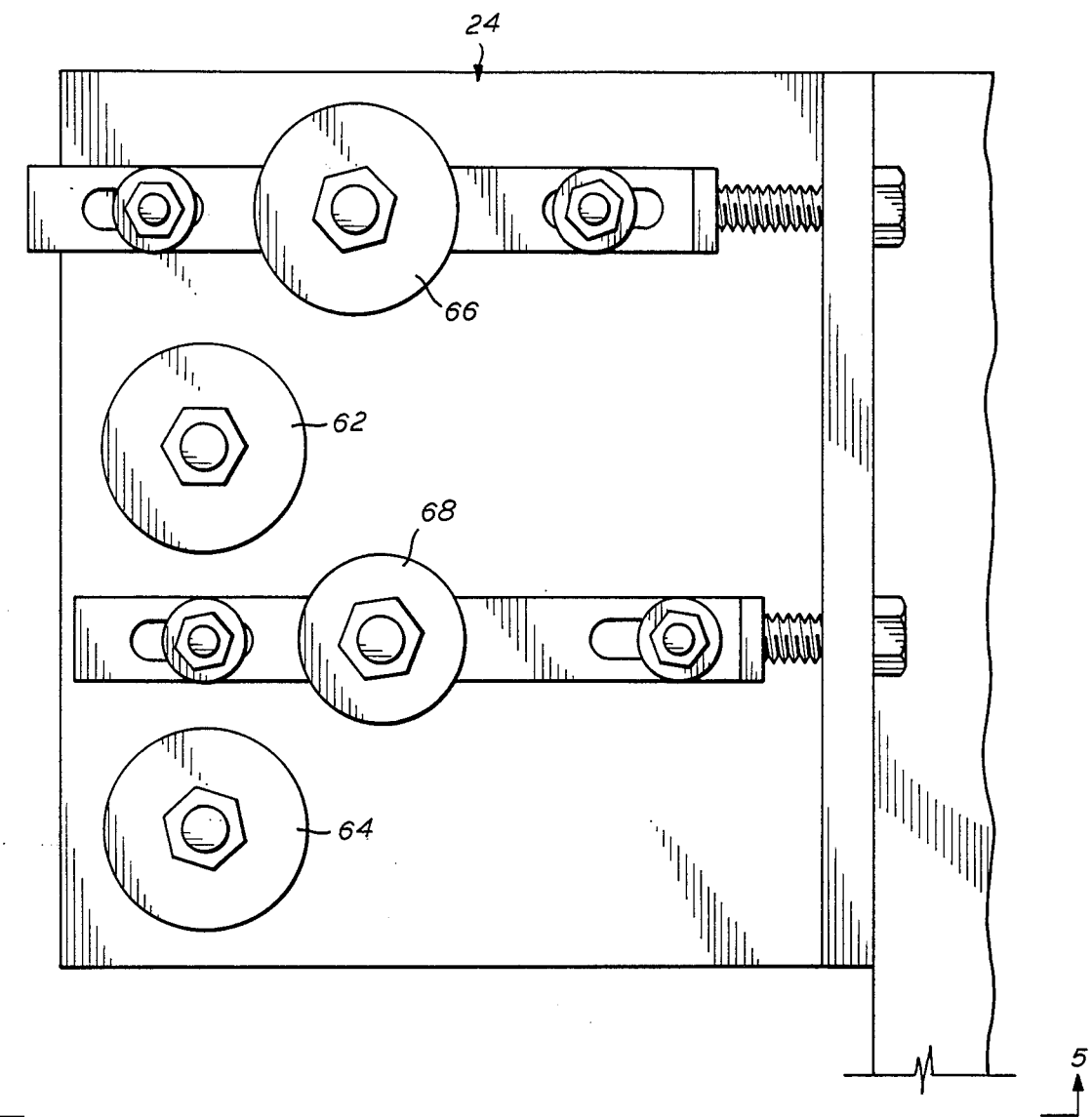
FIG. 4 is an enlarged fragmentary elevational view of the coiling and straightening mechanism.
Figure 5:
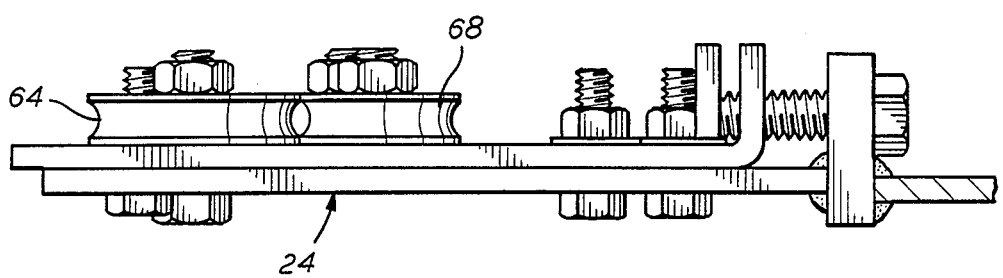
FIG. 5 is a cross-sectional view taken along the line 5—5 of FIG. 4.

Referring now to FIGS. 2, 4 and 5, the coiling and straightening mechanism 24 consists of four rollers 62, 64, 66, and 68. Two of the rollers 62 and 64 are positioned on one side of the tubing 22 and the other two of the rollers 66 and 68 are positioned on the opposite sides of the tubing 22. Rollers 62 and 64 are affixed and rollers 66 and 68 may be adjusted. In coiling the tubing 22 on withdrawing the tubing from the ground, rollers 62, 64 and 66 are utilized and the diameter of the desired coil is provided by the horizontal position of roller 66. On being driven into the ground, rollers 62, 64 and 68 are utilized to straighten the tubing 22. Roller 68 may be adjusted to remove any set in the tubing 22.

As best seen in FIG. 1, the reaction plate 14 provides a means of coupling the ram 30 against the ground surface and while the reaction plate 14 may be held against the ground using any type of anchor or heavy mass it is preferable to mount the soil analyzer 10 from a transportation vehicle 12. By using the piston and cylinder assemblies 16, the reaction plate 14 may be lowered to the ground surface and raise the vehicle 12 off of its springs in order to take full advantage of the weight of the vehicle 12.

Referring now to FIGS. 2 and 6, a tubular support 70 is preferably connected to the lower end of the reaction plate 14 for surrounding the cone 26 and providing a support and guide as the reaction plate 14 is lowered on to the ground surface. This allows the tubular support 70 to be inserted into and penetrate the ground surface which may include roots thereby protecting and guiding the cone 26.

One of the most common soil measurements is by the use of a friction cone. Referring now to FIG. 7, the cone 26 is shown as a friction measuring cone connected to the lower end of the tubing and includes a hollow body 72, a tip 74 and a sleeve 76. The body 72 includes a first 78 and a second 80 strain guage load cell. The tip 74 is connected to the body 72 and upon being driven into the ground actuates both the first and second load cells 78 and 80 to provide a measurement of the load on the tip 74. The friction of the ground is determined by the interaction of the sleeve 76 and the ground and is measured by the second load cell 80 and is determined by subtracting the tip load measurement from the tip plus friction load measurement. The tip 74 may also include a porous portion 82 and a cavity 84 which is in communication with an instrumentated diaphragm 86 which measures the interstitial pore water pressure.

The sleeve 76 is pressed fitted over the load cells 78 and 80 and a shoulder 88 prevents excessive upward travel of the sleeve 76 during penetration. Water is prevented from entering the interior of the body 72 be the use of a silastic sealer between the sleeve 76 and the body 72.

Figure 3:
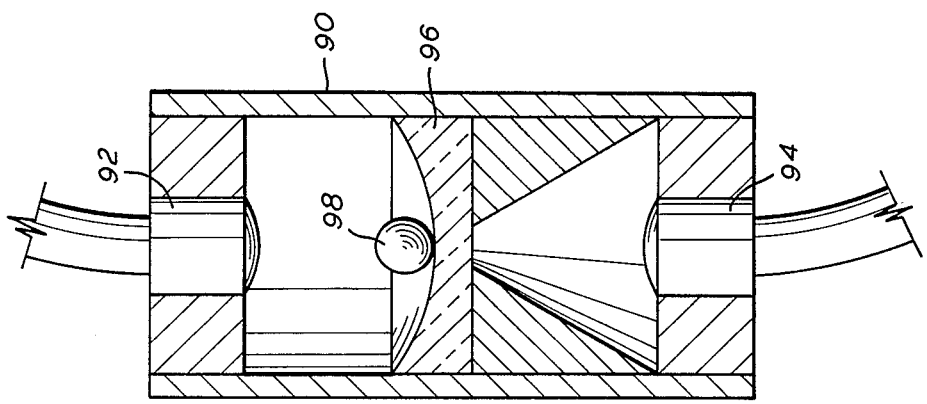
FIG. 3 is an enlarged cross-sectional view of an angle measuring means.

As best seen in FIGS. 3 and 7 a cone angle measuring device 90 may be provided connected to the body 72 and may be an optical tilt meter whrch includes a light source 92, a photosensor 94 and a concave lens 96 psitioned between the light source 92 and 94. A steel ball 98 rides on the concave surface of the lens 96. Therefore, the light from the source 92 is limited in reaching the sensor 94 depending upon the position of the ball 98. As the sensor 90 is tilted, the ball 98 rolls on the concave surface of the lens 96 allowing more light to pass. Therefore, the output from the photosensor 94 is proportional to the angle of tilt of the sensor 90 and thus of the cone 26.

Referring now to FIG. 8, another type of cone 100 is best seen which is of a sniffer type to provide means of locating and quantifyrng contaminants in the soil by sampling the interstitial fluids and/or vapor at different depths. The cone 100 includes a body 102 and a sleeve 104 which telescopically engages the inside of the body 102. The sleeve 104 is of a porous material such as sintered stainless steel or porous plastic thereby providing sampling openings. A tip 106 is supported by a rod 108 having a retaining shoulder 110. In use, the cone 100 may be driven into the ground and then raised allowing the tip 106 and sleeve 104 to move downwardly relative to the body 102. Vacuum can then be applied to the top end of the tubing 22 to withdraw vapor or water for measuring possible contaminants in the soil.

The cone 100 may also be used for grouting to prevent the vertical migration of a contaminant through the sounding hole. In this case, the rod 108 is omitted and the tip 106 is held in position during downward movement by the sleeve 104. At the desired depth, the cone 100 is retracted to expose the porous filter 104 and a sample is taken. After the sampling is complete a grout line is attached to the upper end of the tubing 22 and is pumped down the tubing 22 and cone 100 releasing and leaving the tip 106 in the hole and sealing off any contaminats by the grouting.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will be readily apparent to those skilled in the art and which are encompassed within the spirit of the invention and the scope of the appended claims.

What is claimed is:

1. A soil analyzer for driving into the ground comprising,
   a hydraulic ram having a longitudinal opening therethrough,
   a hollow tubing extending through the opening,
   a two-way chucking mechanism connected to the ram and engaging the outside of the tubing for driving the tubing into the ground and pulling the tubing from the ground,
   a coiling and straightening mechanism positioned above the ram engaging the tubing for coiling the tubing as it is removed from the ground and for straightening the tubing when it is being driven into the ground,
   means connected to the ram for holding the ram against the ground, and
   a cone connected to the bottom end of the tubing for being driven into the ground.

2. The apparatus of claim 1 including,
   a tubular support member connected to the bottom of the ram surrounding the cone and lower end of the tubing for insertion into the surface of the ground for protecting the cone during penetration of hard ground surfaces.

3. The apparatus of claim 1 including, an anti-buckling support positioned in the ram opening and around the tubing for supporting the tube and it is driven downwardly.

4. The apparatus of claim 3 wherein the buckling support includes split tubes having a shoulder for engaging the ram.

5. The apparatus of claim 1 wherein the coiling and straightening mechanism includes four rollers with two of the rollers positioned on one side of the tubing and another two of the rollers positioned on the opposite side of the tubing.

6. The apparatus of claim 1 wherein the cone includes,
   a load cell hollow body having frrst!and second strain gauge load cells,
   a tip connected to the body for actuating the load cells for measuring the driving force on the cone top,
   a sleeve connected to the second load cell whereby the first and second load cells measure the driving force on the tip and the second load cell measures both the driving force on the tip and the friction of the ground on the sleeve.

7. The apparatus of claim 6 including a cone angle measuring means connected to the body comprising,
   a light source,
   a photosensor,
   a concave lens between the source and sensor, and
   a ball movable on the concave lens and varying the amount of light transmitted to the sensor in proportion to the angle of the body.

8. The apparatus of claim 1 wherein the cone includes,
   a body,
   a sleeve telescopically engaging the inside of the body, said sleeve including sampling openings,
   a tip connected to the sleeve, said tip pushing the sleeve into the body when the tip is driven into the ground, and said tip extending the sleeve out of the body for obtaining fluid samples when the cone is pulled upwardly.

9. The apparatus of claim 1 wherein the said analyzer is supported from a vehicle and the means for holding the ram aagainst the ground includes a plate connected to piston and cylinder means connected to the vehicle.

* * * * *

UNITED STATES PATENT OFFICE
CERTIFICATE OF CORRECTION

Patent No. 4,726,239   Dated February 23, 1988

Inventor(s)   Ronald L. Boggess et al.

It is certified that error appears in the above-identified patent and that said Letters Patent are hereby corrected as shown below:

Column 1, line 49, delete "o" and insert -- on --

Column 2, line 33, after "FIG. 8" insert -- is --

Column 3, line 36, delete "instalIed" and insert -- installed --

Column 3, line 39, delete "snoulders" and insert -- shoulders --

Column 3, line 47, delete "lhe" and insert -- the --

Column 3, line 49, delete "y" and insert -- by --

Column 3, line 51, delete "approximatly" and insert -- approximately --

Column 4, line 22, after "tubing" inser -- 22 --

Column 4, line 24, delete "guage" and insert -- gauge --

Column 4, line 40, delete "be" and insert -- by --

Column 4, line 45, delete "whrch" and insert -- which --

Column 4, line 46, delete "psi-" and insert -- posi-"

Column 4, line 58, delete "quantifyrng" and insert -- quantifying --

Column 5, line 10, after "and" insert -- grout --

UNITED STATES PATENT OFFICE
CERTIFICATE OF CORRECTION

Patent No. 4,726,239     Dated February 23, 1988

Inventor(s) Ronald L. Boggess et al.

It is certified that error appears in the above-identified patent and that said Letters Patent are hereby corrected as shown below:

Column 6, line 15, delete "frrst!and" and insert
-- first and --

Column 6, line 45, delete "aagainst" and insert
-- against --

Signed and Sealed this

Twenty-ninth Day of November, 1988

Attest:

DONALD J. QUIGG

Attesting Officer     Commissioner of Patents and Trademarks